US011078357B2

(12) United States Patent
Karube

(10) Patent No.: US 11,078,357 B2
(45) Date of Patent: Aug. 3, 2021

(54) THERMOPLASTIC ELASTOMER COMPOSITION, EXTRUSION MOLDED ARTICLE, AND MEDICAL TUBE

(71) Applicant: MCPP Innovation LLC, Chiyoda-ku (JP)

(72) Inventor: Kanae Karube, Tokyo (JP)

(73) Assignee: MCPP Innovation LLC, Chiyoda-ku (JP)

( * ) Notice: Subject to any disclaimer, the term of this patent is extended or adjusted under 35 U.S.C. 154(b) by 0 days.

(21) Appl. No.: 16/440,491

(22) Filed: Jun. 13, 2019

(65) Prior Publication Data

US 2019/0309157 A1   Oct. 10, 2019

Related U.S. Application Data

(63) Continuation of application No. PCT/JP2017/044680, filed on Dec. 13, 2017.

(30) Foreign Application Priority Data

Dec. 14, 2016 (JP) .............................. JP2016-242366

(51) Int. Cl.

| C08L 53/02 | (2006.01) |
|---|---|
| A61L 29/06 | (2006.01) |
| A61L 29/14 | (2006.01) |
| A61M 39/08 | (2006.01) |
| B29B 9/10 | (2006.01) |
| B29C 48/00 | (2019.01) |
| B29C 48/09 | (2019.01) |
| B29C 48/30 | (2019.01) |
| A61L 29/04 | (2006.01) |
| C08L 23/10 | (2006.01) |
| A61L 31/06 | (2006.01) |
| A61L 31/04 | (2006.01) |
| A61M 5/14 | (2006.01) |
| B29K 96/04 | (2006.01) |
| B29L 23/00 | (2006.01) |

(52) U.S. Cl.
CPC .............. *C08L 53/025* (2013.01); *A61L 29/04* (2013.01); *A61L 29/06* (2013.01); *A61L 29/14* (2013.01); *A61L 31/04* (2013.01); *A61L 31/06* (2013.01); *A61M 5/14* (2013.01); *A61M 39/08* (2013.01); *B29B 9/10* (2013.01); *B29C 48/022* (2019.02); *B29C 48/09* (2019.02); *B29C 48/30* (2019.02); *C08L 23/10* (2013.01); *C08L 53/02* (2013.01); *B29K 2096/04* (2013.01); *B29L 2023/00* (2013.01); *C08L 2205/025* (2013.01); *C08L 2205/035* (2013.01); *C08L 2207/04* (2013.01)

(58) Field of Classification Search
CPC ......... C08L 2205/025; C08L 2205/035; C08L 2207/04; C08L 23/10; C08L 53/02; C08L 53/025; A61L 29/04; A61L 29/049; A61L 29/06; A61L 29/14; A61L 31/04; A61L 31/041; A61L 31/06; A61L 31/14; A61M 39/08; A61M 5/14; B29B 9/10; B29C 48/022; B29C 48/09; B29C 48/30; B29K 2096/04; B29L 2023/00
See application file for complete search history.

(56) References Cited

U.S. PATENT DOCUMENTS

| 10,131,780 | B2 | 11/2018 | Yagi et al. | |
|---|---|---|---|---|
| 2005/0196612 | A1 | 9/2005 | Flood et al. | |
| 2005/0197464 | A1 | 9/2005 | Handlin, Jr. et al. | |
| 2005/0197465 | A1 | 9/2005 | Handlin, Jr. | |
| 2007/0004830 | A1 | 1/2007 | Flood et al. | |
| 2010/0038815 | A1 | 2/2010 | Flood et al. | |
| 2010/0087559 | A1* | 4/2010 | Kusanose | C08F 8/04 521/148 |
| 2010/0239802 | A1* | 9/2010 | Kuwahara | C08L 23/14 428/36.9 |
| 2011/0015333 | A1 | 1/2011 | Fujiwara et al. | |
| 2011/0319837 | A1 | 12/2011 | Uehara et al. | |
| 2013/0225020 | A1 | 8/2013 | Flood et al. | |
| 2013/0299731 | A1 | 11/2013 | Wright et al. | |

(Continued)

FOREIGN PATENT DOCUMENTS

| CN | 1233627 A | 11/1999 |
|---|---|---|
| CN | 1946798 A | 4/2007 |

(Continued)

OTHER PUBLICATIONS

International Search Report dated Mar. 20, 2018 in PCT/JP2017/044680 filed Dec. 13, 2017 (with English Translation).
Extended European Search Report dated Dec. 4, 2019 in Patent Application No. 17882129.4, 10 pages.
Notification of Reason for Refusal dated Feb. 15, 2021, in Korean Patent Application No. 10-2019-7016947 filed Dec. 13, 2017 (with English translation).
Office Action dated Apr. 6, 2021, in Japanese Patent Application No. 2017-238824 filed Dec. 13, 2017 (with machine generated English translation).

(Continued)

*Primary Examiner* — Yan Lan
(74) *Attorney, Agent, or Firm* — Oblon, McClelland, Maier & Neustadt, L.L.P.

(57) ABSTRACT

An object of the present invention is to provide a thermoplastic elastomer composition capable of molding a medical tube excellent in the transparency and kink resistance. The present invention is related to a thermoplastic elastomer composition including a hydrogenated block copolymer (A) wherein the copolymer has at least two polymer blocks P composed mainly of an aromatic vinyl compound unit and at least one polymer block Q composed mainly of a conjugated diene compound unit; the total content of aromatic vinyl compound units is from 8 to 25% by mass; and the copolymer contains a high-MFR hydrogenated block copolymer and a propylene polymer (B).

20 Claims, No Drawings

(56) References Cited

U.S. PATENT DOCUMENTS

| | | |
|---|---|---|
| 2013/0331519 A1 | 12/2013 | Sawasato et al. |
| 2014/0364532 A1 | 12/2014 | Dubois et al. |
| 2014/0364555 A1 | 12/2014 | Wiegand et al. |
| 2014/0371377 A1 | 12/2014 | Salazar |
| 2016/0102164 A1 | 4/2016 | Wiegand et al. |
| 2016/0222258 A1 | 8/2016 | Sustic et al. |
| 2016/0230000 A1 | 8/2016 | Gu |
| 2017/0029614 A1 | 2/2017 | Yagi et al. |

FOREIGN PATENT DOCUMENTS

| | | |
|---|---|---|
| CN | 101796131 A | 8/2010 |
| CN | 101970573 A | 2/2011 |
| CN | 102348756 A | 2/2012 |
| CN | 106170515 A | 11/2016 |
| EP | 2 258 771 A1 | 12/2010 |
| EP | 2 407 512 A1 | 1/2012 |
| JP | 2000-7846 | 1/2000 |
| JP | 2000-204261 | 7/2000 |
| JP | 2003-287163 | 10/2003 |
| JP | 2005-247895 | 9/2005 |
| JP | 2007-526387 | 9/2007 |
| JP | 2007-526388 A | 9/2007 |
| JP | 2013-199618 A | 10/2013 |
| JP | 2013-203991 A | 10/2013 |
| JP | 2015-513584 | 5/2015 |
| JP | 2016-145303 | 8/2016 |
| JP | 2016-530355 A | 9/2016 |
| WO | 2010/104068 A1 | 9/2010 |
| WO | 2012/117964 A1 | 9/2012 |

OTHER PUBLICATIONS

Information Offer Form dated Mar. 23, 2021, in Japanese Patent Application No. 2017-238824 filed Dec. 13, 2017 (with English translation).

Kraton Polymer Product Catalog, p. 12 (with English translation) (front cover, p. 12 and back cover).

Office Action dated Jun. 10, 2021, in Chinese Patent Application No. 201780077206.6 filed Dec. 13, 2017 (with English translation).

Decision of Refusal dated Jun. 15, 2021, in Japanese Patent Application No. 2017-236624 filed Dec. 13, 2017 (with English translation).

* cited by examiner

THERMOPLASTIC ELASTOMER COMPOSITION, EXTRUSION MOLDED ARTICLE, AND MEDICAL TUBE

TECHNICAL FIELD

The present invention is related to a thermoplastic elastomer composition suitable as a material of a medical tube such as transfusion set tube, extension tube, blood circuit tube, feeding tube, connecting tube and catheter, and an extrusion molded body and a medical tube each formed from the thermoplastic elastomer.

BACKGROUND ART

The medical tube such as transfusion set tube, extension tube, blood circuit tube, feeding tube, connecting tube and catheter is required to have flexibility. On the other hand, it is required to have kink resistance (bending resistance) so as not to form a dam for stopping an internally flowing liquid when the tube is curved. With respect to this kink resistance, it is desired that the force required to curve the tube (kink force) is large and the kink radius (a radius to which the tube can be curved) is small.

The medical tube is also required to have excellent transparency so that, in addition to visual cleanliness and hygiene, for example, the type (color) of the internally flowing liquid, the flow state, or whether a liquid is present or not can be easily confirmed with an eye.

Conventionally, a soft vinyl chloride resin has been used as the material of medical tubes. However, the soft vinyl chloride resin contains a large amount of a plasticizer such as dioctyl phthalate, which gives rise to a problem that the plasticizer in the medical tube is eluted to contaminate the liquid flowing inside the medical tube.

Accordingly, in recent years, studies are being made on use of a styrene elastomer as a replacement of the soft vinyl chloride resin, and Patent Literature 1 suggests a medical resin composition obtained by blending a hydrogenated block copolymer satisfying specific conditions and an olefin resin. Although Patent Literature 1 is silent on the preferable range of MFR of the hydrogenated block copolymer used, in Examples, those having MFR (JIS K7210) of 3.5 to 10 g/10 min were used. In addition, in Patent Literature 1, although the kink resistance was evaluated, the evaluation of transparency was not performed.

Patent Literature 2 suggests, as a propylene random copolymer composition having an excellent balance of flexibility, transparency and low stickiness, a composition containing a specific propylene random copolymer and a hydrogenated block copolymer, and it is described that the composition is applicable to a medical tube. Furthermore, Patent Literature 2 discloses that the MFR (ISO 1133) of the hydrogenated block copolymer used is from 0.1 to 12 g/10 min and is most preferably from 1.0 to 5 g/10 min.

In Patent Literature 2, although the transparency was evaluated by the haze, evaluation of the transparency as a medical tube is not sufficient only using the haze. Additionally, since the apparent transparency may be reduced due to diffused reflection of light on the tube surface having high surface roughness, it is important to evaluate the transparency by the surface roughness.

Furthermore, with respect to the kink resistance, it is also suitable for the evaluation of kink resistance as a medical tube by the method using a tensile tester described later in the paragraph of Examples rather than by the evaluation methods of Patent Literatures 1 and 2.

CITATION LIST

Patent Literature

Patent Literature 1: JP-A-2005-247895
Patent Literature 2: JP-A-2016-145303

SUMMARY OF INVENTION

Technical Problem

As a result of studies by the present inventors, it has been revealed that both the compositions described in Patent Literatures 1 and 2 are insufficient in the transparency evaluated by the surface roughness and the kink resistance evaluated using a tensile tester.

This is considered to result because in the compositions described in Patent Literatures 1 and 2, the hydrogenated block copolymer used has low MFR, and surface roughening occurs during extrusion molding, which leads to a reduction in the transparency and at the time of bending, generation of a kink originating from the surface roughness.

An object of the present invention is to solve the problems of the above-described conventional thermoplastic elastomer compositions for medical tubes and provide a thermoplastic elastomer composition capable of molding a medical tube excellent in the transparency and kink resistance, and an extrusion molded body and a medical tube each formed from the thermoplastic elastomer composition.

Solution to Problem

The present inventors have made many intensive studies to achieve the object above and found that when a copolymer having high MFR is used as the hydrogenated block copolymer contained in a thermoplastic elastomer and a propylene polymer is blended therewith, a medical tube excellent in the transparency and kink resistance can be obtained. The present invention has been accomplished based on the finding.

Namely, summary of the present invention is described in the following [1] to [10].

[1] A thermoplastic elastomer composition containing a hydrogenated block copolymer (A) and a propylene polymer (B), wherein the hydrogenated block copolymer (A) is a hydrogenated product of a block copolymer having at least two polymer blocks P composed mainly of an aromatic vinyl compound unit and at least one polymer block Q composed mainly of a conjugated diene compound unit;

a total content of the aromatic vinyl compound unit in the hydrogenated block copolymer (A) is from 8 to 25% by mass; and the thermoplastic elastomer composition contains, as the hydrogenated block copolymer (A), a high-MFR hydrogenated block copolymer having a melt flow rate (MFR) of 40 to 300 g/10 min as measured in accordance with ISO 1133 at 230° C. under a load of 2.16 kg.

[2] The thermoplastic elastomer composition according to the above [1], wherein the polymer block P contains a styrene unit as a main constituent unit; and the polymer block Q contains a butadiene unit as a main constituent unit, in the high-MFR hydrogenated block copolymer, and a proportion of 1,2-bond in the butadiene unit is 60% by weight or more.

[3] The thermoplastic elastomer composition according to the above [1] or [2], further containing, as the hydrogenated block copolymer (A), a low-MFR hydrogenated block copolymer having a melt flow rate (MFR) of 0.5 to 39 g/10 min as measured in accordance with ISO 1133 at 230° C. under a load of 2.16 kg.

[4] The thermoplastic elastomer composition according to the above [3], wherein a content of the low-MFR hydrogenated block copolymer per 100 parts by weight of the high-MFR hydrogenated block copolymer is from 10 to 500 parts by weight.

[5] The thermoplastic elastomer composition according to any one of the above [1] to [4], wherein per 100 parts by weight of a total of the hydrogenated block copolymer (A) and the propylene polymer (B), a content of the hydrogenated block copolymer (A) is from 30 to 95 parts by weight and a content of the propylene polymer (B) is from 5 to 70 parts by weight.

[6] The thermoplastic elastomer composition according to any one of the above [1] to [5], wherein 80 mol % or more of the conjugated diene compound units contained in the hydrogenated block copolymer (A) are hydrogenated.

[7] The thermoplastic elastomer composition according to any one of the above [1] to [6], which is a molding material for a medical tube.

[8] An extrusion molded body of the thermoplastic elastomer composition according to any one of the above [1] to [7].

[9] The extrusion molded body according to the above 8, which has a tube shape.

[10] A medical tube formed from the thermoplastic elastomer composition according to any one of the above [1] to [7].

Effects of Invention

According to the thermoplastic elastomer composition of the present invention, an extrusion molded body and a medical tube each being excellent in the transparency and kink resistance are provided.

DESCRIPTION OF EMBODIMENTS

The present invention is described in detail below. The following description is an example of the embodiment of the present invention, and the present invention is not limited to the contents described below as long as its gist is observed, and can be implemented by arbitrarily making changes therein without departing from the gist of the present invention.

Here, in the present invention, numerical or physical property values expressed by inserting "to" therebetween are used to include the values before and after "to". In addition, "% by weight" and "parts by weight" have the same meanings as "% by mass" and "parts by mass", respectively.

In the present invention, the melt flow rate (MFR) and the flexural modulus are values measured as follows.

<MFR>

The MFR of the hydrogenated block copolymer (A) is measured in accordance with ISO 1133 under the conditions of a temperature of 230° C., a load of 2.16 kg, and 10 minutes.

The MFR of the propylene polymer (B) is measured in accordance with JIS K7210:1999 under the conditions of a temperature of 230° C., a load of 2.16 kg, and 10 minutes.

<Flexural Modulus>

The flexural modulus of the propylene polymer (B) is measured in accordance with JIS K7171:2008.

Furthermore, in the present invention, the "unit" in a polymer or a polymer block indicates a constituent unit derived from a raw material compound and formed in a polymer obtained as a result of polymerization of the raw material compound. For example, an aromatic vinyl compound unit is a unit per an aromatic vinyl compound, which is produced as a result of polymerization of an aromatic vinyl compound, and a conjugated diene compound unit is a unit per a conjugated diene compound, which is produced as a result of polymerization of a conjugated diene compound.

[Thermoplastic Elastomer Composition]

The thermoplastic elastomer composition of the present invention is a thermoplastic elastomer composition including a hydrogenated block copolymer (A) and a propylene polymer (B), wherein the hydrogenated block copolymer (A) is a hydrogenated product of a block copolymer having at least two polymer blocks P composed mainly of an aromatic vinyl compound unit and at least one polymer block Q composed mainly of a conjugated diene compound unit; the total content of aromatic vinyl compound units in the hydrogenated block copolymer (A) is from 8 to 25% by mass; and the composition contains, as the hydrogenated block copolymer (A), a high-MFR hydrogenated block copolymer having a melt flow rate (MFR) of 40 to 300 g/10 min as measured in accordance with ISO 1133 at 230° C. under a load of 2.16 kg. In addition, the composition is characterized by preferably further including, together with the high-MFR hydrogenated block copolymer, a low-MFR hydrogenated block copolymer having a melt flow rate (MFR) of 0.5 to 39 g/10 min as measured in accordance with ISO 1133 at 230° C. under a load of 2.16 kg.

[Mechanism]

Since the thermoplastic elastomer composition of the present invention contains, as the hydrogenated copolymer (A), a high-MFR hydrogenated copolymer having an MFR (ISO 1133 (230° C., load: 2.16 kg)) of 40 to 300 g/10 min, the flow of the resin during extrusion molding is stabilized, and this is effective in smoothing the extrusion molded article surface. In addition, together with the high-MFR hydrogenated block copolymer, a low-MFR hydrogenated bock copolymer having an MFR (ISO 1133 (230° C., load: 2.16 kg)) of 0.5 to 39 g/10 min is contained as the hydrogenated block copolymer (A), and the shapability of the extrusion molded article can thereby be enhanced.

Furthermore, a propylene polymer (B) is contained together with the hydrogenated block copolymer (A) containing a high-MFR hydrogenated block copolymer and preferably further containing a low-MFR hydrogenated block copolymer, which makes it possible to impart shapability at the time of extrusion molding with maintaining the transparency of the molded article and impart sterilization resistance which does not involve a change in the shape and surface condition, stickiness, etc. before and after sterilization of the medical tube.

By virtue of these effects, according to the thermoplastic elastomer composition of the present invention, a medical tube excellent in the transparency and kink resistance can be molded.

[Hydrogenated Block Copolymer (A)]

The hydrogenated block copolymer (A) used in the present invention (hereinafter, sometimes referred to as "component (A)") has at least two polymer blocks P (hereinafter, sometimes simply referred to as "block P") composed mainly of an aromatic vinyl compound unit and at least one polymer block Q (hereinafter, sometimes simply referred to as "block Q") composed mainly of a conjugated diene compound unit. In other words, the hydrogenated block copolymer (A) is a hydrogenated block copolymer in which a block copolymer having at least two blocks P and at least one block Q is hydrogenated (hydrogen-added).

The term "composed mainly of" as used herein means to contain 50 mol % or more of the target monomer unit in the target polymer block.

The aromatic vinyl compound constituting the block P is not particularly limited and includes, for example, an aromatic vinyl compound such as styrene, α-methylstyrene, p-methylstyrene, divinylbenzene, 1,1-diphenylethylene, N,N-dimethyl-p-aminoethyl styrene and N,N-diethyl-p-aminoethylstyrene. Among these, in view of availability and productivity, styrene, α-methylstyrene, and p-methylstyrene are preferably used. In particular, styrene is preferred.

The block P may consist of one type of an aromatic vinyl compound unit or may consist of two or more types of aromatic vinyl compound units. In addition, the block P may contain a monomer unit other than the aromatic vinyl compound unit.

The conjugated diene compound constituting the block Q is a diolefin having a pair of conjugated double bonds and includes for example, but is not limited to, 1,3-butadiene, 2-methyl-1,3-butadiene (isoprene), 2,3-dimethyl-1,3-butadiene, 1,3-pentadiene, 2-methyl-1,3-pentadiene, and 1,3-hexadiene. Among these, in view of availability and productivity, 1,3-butadiene and isoprene are preferably used. In particular, 1,3-butadiene is preferred.

The block Q may consist of one type of a conjugated diene compound unit or may consist of two or more types of conjugated diene compound units. In addition, the block Q may contain a monomer unit other than the conjugated diene compound unit.

The block polymer before hydrogenation, having at least two blocks P and at least one block Q, may be any of linear, branched, radial, etc. but is preferably a block copolymer represented by the following formula (1) or (2):

P-(Q-P)m                                    (1)

(P-Q)n                                      (2)

wherein P and Q represent block P and block Q, respectively; m represents an integer of 1 to 5; and n represents an integer of 2 to 5, and in the case where a plurality of blocks are present with respect to each of the block P and the block Q, the compound units thereof may be the same as or different from one another.

In formula the (1) or (2), m and n are preferably larger from the viewpoint of lowering the order-disorder transition temperature as a rubbery polymer body but are preferably smaller in terms of ease of manufacturing and cost.

In view of rubber elasticity of the composition and kink resistance of the molded article, the hydrogenated block copolymer (A) is preferably a hydrogenated product of a block copolymer represented by the formula (1); more preferably a hydrogenated product of a block copolymer represented by the formula (1) in which m is 3 or less; still more preferably a hydrogenated product of a block copolymer represented by the formula (1) in which m is 2 or less; and most preferably a hydrogenated product of a block copolymer represented by the formula (1) in which m is 1.

The content of all aromatic vinyl compound units (the total content of aromatic vinyl compound units) in the hydrogenated block copolymer (A) is from 8 to 25% by mass; preferably from 9 to 21% by mass; more preferably from 10 to 20% by mass; and still more preferably from 10 to 19% by mass.

The content of all aromatic vinyl compound units in the hydrogenated block copolymer (A) is 8% by mass or more, since the obtained thermoplastic elastomer composition and an extrusion molded body and a medial tube each using the composition need to maintain low stickiness and tearing strength. On the other hand, in view of the flexibility, transparency and kink resistance of the obtained thermoplastic elastomer composition and an extrusion molded body and a medial tube each using the composition, among others, with respect to the transparency, if the content exceeds 25% by mass, the effect of the present invention of satisfying both kink resistance and transparency is not exerted. For this reason, the content must be 25% by mass or less.

In view of the flexibility, transparency, low stickiness and strain recoverability of the obtained thermoplastic elastomer composition and an extrusion molded body and a medial tube each using the composition, the content of the block P (total amount of blocks P) in the hydrogenated block copolymer (A) is preferably from 8 to 25% by mass; more preferably from 9 to 20% by mass; and still more preferably from 10 to 19% by mass.

In addition, the content of the block Q (total amount of polymer blocks Q) in the hydrogenated block copolymer (A) is preferably from 75 to 92% by mass; more preferably from 80 to 91% by mass; and still more preferably from 81 to 90% by mass.

With respect to the hydrogenated block copolymer (A) used in the present invention, it is preferred that 80 mol % or more of all conjugated diene compound units in the hydrogenated copolymer (A) are hydrogenated.

The hydrogenation rate of all conjugated diene compound units contained in the hydrogenated block copolymer (A) (hereinafter, this hydrogenation rate is sometimes simply referred to as "hydrogenation rate"), namely, the hydrogenation rate of carbon-carbon double bond of the conjugated diene compound unit, is preferably 80 mol % or more; more preferably 85 mol % or more; and still more preferably 90 mol % or more.

When the hydrogenation rate is 80 mol % or more, the value of dissolution parameter comes close to that of the propylene polymer (B), and good dispersion is obtained, which leads to a tendency that the flexibility, transparency, low stickiness, kink resistance and strain recoverability of the obtained thermoplastic elastomer composition and an extrusion molded body and a medial tube each using the composition are improved. The hydrogenation rate can be measured by the proton nuclear magnetic resonance ($^1$H-NMR) method.

Note that in the present description, the conjugated diene compound unit is referred to as "conjugated diene compound unit" irrespective of before or after hydrogenation.

In view of the flexibility, transparency, kink resistance and strain recoverability of the obtained thermoplastic elastomer composition and an extrusion molded body and a medial tube each using the composition, the 1,2-bond content (hereinafter, sometimes referred to as "vinyl bond content") in all conjugated diene compound units contained in the block copolymer before hydrogenation of the hydrogenated block copolymer (A) is preferably 60% by mass or more; more preferably 63% by mass or more; and still more preferably 65% by mass or more. In view of productivity, the upper limit value of the vinyl bond content is 95% by mass or less; and preferably 93% by mass or less.

Above all, with respect to the hydrogenated block copolymer (A), it is preferred that the vinyl bond content is from 70 to 93% by mass and 90 mol % or more of all conjugated diene compound units contained in the hydrogenated block copolymer (A) are hydrogenated, namely, the hydrogenation rate is 90 mol % or more.

Here, the vinyl bond content is defined as the proportion, before hydrogenation, of the conjugated diene compound incorporated with 1,2-bond out of those incorporated in the binding modes of 1,2-bond and 1,4-bond. The vinyl bond content in all conjugated diene compound units contained before hydrogenation can be measured by the proton nuclear magnetic resonance (1H-NMR) method.

The method for producing the component (A) in the present invention is not particularly limited and may be any method as long as it is a method in which the above-described structure and physical properties are obtained. The block copolymer before hydrogenation can be obtained, for example, by performing block polymerization in an inert solvent with use of a lithium catalyst, etc. according to the method described in JP-B-S40-23798. In addition, the hydrogenation of the block copolymer can, for example, be performed in the presence of a hydrogenation catalyst in an inert solvent according to the methods described in JP-B-S42-8704, JP-B-S43-6636, JP-A-S59-133203, JP-A-S60-79005, etc.

The present invention is characterized by containing, as the component (A), a high-MFR hydrogenated block copolymer having an MFR (ISO 1133 (230° C., load: 2.16 kg)) of 40 to 300 g/10 min, out of the above-described hydrogenated block copolymers, and preferably using the high-MFR hydrogenated block copolymer in combination with a low-MFR hydrogenated block copolymer having an MFR (ISO 1133 (230° C., load: 2.16 kg)) of 0.5 to 39 g/10 min.

From the viewpoint of more effectively obtaining the effect based on the high-MFR hydrogenated bock copolymer and furthermore, the effect due to combination use with a low-MFR hydrogenated block copolymer, the MFR (ISO 1133 (230° C., load: 2.16 kg) of the high-MFR hydrogenated block copolymer is preferably from 50 to 280 g/10 min, and more preferably from 80 to 250 g/10 min.

With respect to the high-MFR hydrogenated block copolymer, it is particularly preferred that the polymer block P contains a styrene unit as a main constituent unit; the polymer block Q contains a butadiene unit as a main constituent unit; and the proportion of 1,2-bond (vinyl bond content) in the butadiene unit is 60% by mass or more.

In addition, from the viewpoint of more effectively obtaining the effect based on the low-MFR hydrogenated bock copolymer and furthermore, the effect due to combination use with a high-MFR hydrogenated block copolymer, the MFR (ISO 1133 (230° C., load: 2.16 kg) of the low-MFR hydrogenated block copolymer is preferably from 1 to 39 g/10 min; more preferably from 1.5 to 35 g/10 min; and still more preferably from 2.0 to 30 g/10 min. Furthermore, the difference in MFR (ISO 1133 (230° C., load: 2.16 kg) between the high-MFR hydrogenated block copolymer and the low-MFR hydrogenated block copolymer is preferably from 15 to 250 g/10 min; more preferably from 30 to 240 g/10 min; and still more preferably from 50 to 220 g/10 min.

In this connection, the MFR (ISO 1133 (230° C., load: 2.16 kg) of the hydrogenated block copolymer (A) can be controlled by appropriately setting various conditions in the production of the hydrogenated block copolymer, such as amount added of monomer, temperature during polymerization and polymerization time, and thereby controlling the molecular weight of the polymer.

The high-MFR hydrogenated block copolymer and the low-MFR hydrogenated block copolymer are preferably used such that the ratio of the low-MFR hydrogenated copolymer to 100 parts by mass of the high-MFR hydrogenated block copolymer is from 10 to 500 parts by mass; particularly from 30 to 400 parts by mass; and above all, from 50 to 350 parts by mass. When the content ratio of the low-MFR hydrogenated copolymer to the high-MFR hydrogenated block copolymer is in the range above, the effect of the present invention due to combination use of the high-MFR hydrogenated block copolymer and the low-MFR hydrogenated block copolymer can be more unfailingly obtained.

In this connection, with respect to each of the high-MFR hydrogenated block copolymer and the low-MFR hydrogenated block copolymer, one type of a copolymer may be used, or two or more types of copolymers differing in MFR, copolymerization component, hydrogenation rate, etc. may be used as a mixture.

As these high-MFR hydrogenated block copolymer and low-MFR hydrogenated block copolymer, a commercially available product may be used, and, for example, a relevant product selected from "Kraton (registered trademark)" series produced by Kraton Polymer Corporation, "Hybrar (registered trademark)" series produced by Kuraray Corporation, and "Tuftec (registered trademark)" series produced by Asahi Kasei Corporation may be used.

[Propylene Polymer (B)]

The propylene polymer (B) (hereinafter, sometimes referred to as "component (B)") used in the present invention may be sufficient if it is a polymer containing a propylene unit as a main component in a ratio of 50% by mass or more relative to the monomer units constituting the propylene polymer (B), and the polymer may be a homopolymer or copolymer of propylene, but is preferably a propylene random copolymer obtained by the copolymerization of propylene and a monomer other than propylene, in which the monomer units other than propylene are randomly incorporated into the propylene unit chain and the monomer units other than propylene form substantially no chain.

The propylene random copolymer is preferably a copolymer in which the propylene unit content is less than 98% by mass, and suitable examples of the propylene polymer (B) include a random copolymer of propylene and ethylene, and a random copolymer of propylene and an α-olefin having from 4 to 20 carbon atoms.

In the case where a random copolymer of propylene and ethylene or a random copolymer of propylene and an α-olefin having from 4 to 20 carbon atoms is used as the propylene random copolymer, the flexibility, transparency, impact resistance, heat resistance and kink resistance tend to be more improved. The α-olefin includes for example, but is not limited to, 1-butene, 1-pentene, 3-methyl-1-butene, 1-hexene, 3-methyl-1-pentene, 4-methyl-1-pentene, 1-heptene, 1-octene, 1-nonene, 1-decene, 1-dodecene, 1-tetradecene, 1-hexadecene, 1-octadecene, and 1-eicosene. An α-olefin having from 4 to 8 carbon atoms is preferred, and examples thereof include 1-butene, 3-methyl-1-butene, 1-hexene, and 4-methyl-1-pentene. With respect to the ethylene or α-olefin, one type may be used alone, or two or more types may be used in combination.

Among the propylene random copolymers described above, in view of the flexibility, transparency, impact resistance, heat resistance and kink resistance of the obtained thermoplastic elastomer composition and an extrusion molded body and a medial tube each using the composition, a propylene-ethylene random copolymer, a propylene-1- butene random copolymer, and a propylene-ethylene-1-butene ternary random copolymer are more preferred, and it is particularly preferable to use a propylene-ethylene random copolymer.

In view of the flexibility, transparency, low stickiness, impact resistance, heat resistance and kink resistance, the propylene random copolymer as the component (B) is preferably a random copolymer of propylene and ethylene and/or an α-olefin having from 4 to 12 carbon atoms, where in the propylene polymer (B), the content of ethylene and/or α-olefin unit is from 2 to 40% by mass and the content of the propylene unit is from 60 to 98% by mass. From the same viewpoint as above, the content of ethylene and/or α-olefin unit is more preferably from 2 to 30% by mass; still more preferably from 2.5 to 25% by mass; and yet still more preferably from 3 to 20% by mass. The content of the propylene unit is more preferably from 70 to 98% by mass; still more preferably from 75 to 97.5% by mass; and yet still more preferably from 80 to 97% by mass.

The propylene unit content, ethylene unit content and α-olefin unit content in the propylene polymer (B) can be measured by the carbon nuclear magnetic resonance ($^{13}$C-NMR) method.

In view of the processability of the obtained thermoplastic elastomer composition, the MFR (JIS K7210:1999 (230° C., load: 2.16 kg)) of the propylene polymer (B) is preferably from 0.1 to 100 g/10 min; more preferably from 0.5 to 50 g/10 min; still more preferably from 0.8 to 40 g/10 min and yet still more preferably from 1 to 30 g/10 min.

Although the catalyst for use in the production of the propylene polymer (B) is not particularly limited, for example, a polymerization method using a stereoregular catalyst is preferred. The stereoregular catalyst includes for example, but is not limited to, a Ziegler catalyst and a metallocene catalyst. Among these catalysts, a metallocene catalyst is preferred in view of the elution and hygiene of the obtained thermoplastic elastomer composition, extrusion molded body and medical tube.

The Ziegler catalyst includes for example, but is not limited to, a titanium halide compound such as titanium trichloride; titanium tetrachloride; and trichloroethoxytitanium, a two-component catalyst consisting of a transition metal component such as a contact product of the titanium halide compound above with a magnesium compound typified by magnesium halide and an organic metal component such as an alkylaluminum compound or its halide; hydride; alkoxide; etc., and a three-component catalyst obtained by adding an electron-donating compound containing nitrogen, carbon, phosphorus, sulfur, oxygen, silicon, etc. to those components.

The metallocene catalyst includes for example, but is not limited to, a catalyst consisting of a transition metal compound (so-called a metallocene compound) in Group IV of the periodic table containing a ligand having a cyclopentadienyl skeleton, a promoter capable of activation into a stable ionic state by reacting with a metallocene compound, and if desired, an organoaluminum compound, and any known catalyst can be used. The metallocene compound is preferably a crosslinked metallocene compound capable of stereoregular polymerization of propylene, more preferably a crosslinked metallocene compound capable of polymerization of propylene with isotactic regularity.

The production method for the propylene polymer (B) includes, for example, a slurry method using an inert solvent in the presence of the catalyst above, a solution method, a gas phase method using substantially no solvent, and a bulk polymerization method using a polymerization monomer as a solvent.

For example, in the case of a slurry polymerization method, the polymerization can be performed in an inert hydrocarbon such as such as n-butane; isobutene; n-pentane; isopentane; hexane; heptane; octane; cyclohexane; benzene; toluene; and xylene, or a liquid monomer. The polymerization temperature is usually from −80 to 150° C. and preferably from 40 to 120° C. The polymerization pressure is preferably from 1 to 60 atm, and the molecular weight of the obtained propylene polymer (B) can be adjusted with hydrogen or other known molecular weight regulators. The polymerization may be performed by a continuous or batch reaction, and the conditions therefor may be conditions that are usually employed. Furthermore, the polymerization reaction may be performed in a single step or in multiple steps.

With respect to the propylene polymer (B), only one type of a polymer may be used, or two or more types of polymers differing in the copolymerization composition, physical properties, etc. may be used as a mixture.

As the propylene random copolymer of the component (B), a commercially available product may be used, and, for example, a relevant product selected from "RANPLEN" produced by Lotte Chemical Corporation, and "NOVATEC (registered trademark) PP", "WINTEC (registered trademark)" and "WELNEX (registered trademark)" series produced by Japan Polypropylene Corporation may be used.

[Ratio of Component (A) and Component (B)]

The thermoplastic elastomer composition of the present invention preferably contains from 30 to 95 parts by mass of the component (A) and from 5 to 70 parts by mass of the component (B), per 100 parts by mass of a total of the hydrogenated block copolymer (A) as the component (A) and the propylene polymer (B) as the component (B). In view of the mechanical strength and heat resistance of the obtained thermoplastic elastomer composition and the shapability during extrusion molding, it is preferred that the content of the component (A) is not more than the upper limit in the range above and the content of the component (B) is not less than the lower limit in the range above. On the other hand, in view of the transparency and sterilization resistance of the obtained thermoplastic elastomer composition and the flexibility and kink resistance of the tube molded article, it is preferred that the content of the component (A) is not less than the lower limit in the range above and the content of the component (B) is not more than the upper limit in the range above.

In order to still further improve the required properties, it is more preferred that the content of the component (A) is from 32 to 92 parts by mass and the content of the component (B) is from 8 to 68 parts by mass, per 100 parts by mass of a total of the component (A) and the component (B); and it is still more preferred that the content of the component (A) is from 35 to 90 parts by mass and the content of the component (B) is from 10 to 65 parts by mass.

[Other Components]

The thermoplastic elastomer composition may contain other components, if desired, in addition to the component (A) and the component (B). Other components are not particularly limited and include, for example, an additive for resins, such as flame retardant, stabilizer, colorant, pigment, antioxidant, antistatic agent, dispersant, flow enhancer, mold release agent (e.g., metal stearate, amide), silicone oil, mineral oil-based softener, synthetic resin-based softener, copper inhibitor, crosslinking agent, nucleating agent and antiblocking agent for pellets. A required amount of other components are added and blended in the range of usually 1 part by mass per 100 parts by mass of a total of the component (A) and the component (B).

[Production Method of Thermoplastic Elastomer Composition]

The thermoplastic elastomer composition of the present invention can be produced, for example, by a method of dry-blending the hydrogenated block copolymer (A), the propylene polymer (B), and other components added as needed, according to the composition ratio of respective components, or a method of preparing the composition by means of a device used for mixing of usual polymeric substances. The mixing device used here is not particularly limited but includes, for example, a kneader such as Banbury mixer, Labo Plastomill, single-screw extruder and twin-screw extruder. Of these, in view of productivity and good kneadability, the composition is preferably produced by a melt-mixing method using an extruder. The melting temperature during kneading may be appropriately set but is usually from 130 to 300° C., and preferably from 150 to 250° C.

[Extrusion Molded Body]

A tube-shaped extrusion-molded body (hereinafter, sometimes referred to as a tube-shaped molded body or an extruded tube) can be obtained by melt-extrusion molding of the thermoplastic elastomer composition of the present invention.

However, the thermoplastic elastomer composition of the present invention is not limited to use in melt-extrusion molding into a tube shape and is also applicable to forming a sheet-shaped or film-shaped molded body by melt-extrusion molding, inflation molding, blow molding, press molding, etc.

In view of the effect of transparency and kink resistance due to the thermoplastic elastomer composition of the present invention, the thermoplastic elastomer composition of the present invention is more effective as a molding material for a tube-shaped molded body.

As the evaluation of transparency of the tube-shaped molded body, a value of the surface roughness (arithmetic average roughness Ra, ten-points average roughness Rz) of the extruded tube as measured using a surface roughness profilometer under the conditions described later in Examples can be used. If the value of surface roughness is large, light is likely to be diffusively reflected from the tube surface and therefore, the transparency of the tube is reduced.

For use as a medical tube, in view of visibility of the contents, the transparency is preferably high, and it is preferred that Ra is 0.5 or less and Rz is 1 or less.

As the evaluation of kink resistance of the tube-shaped molded body, values of the kink force and kink radius of the extruded tube as measured using a tensile tester under the conditions described later in Examples can be used.

For use as a medical tube, it is preferred that the force required to kinking is large and the kink radius is small, and it is preferred that the test force at the time of kinking is 0.3 N or more and the kink radius is 30 mm or less.

The tube-shaped molded body of the present invention is excellent in the transparency and kink resistance and by making use of these properties, can be suitably used for a wide range of applications such as home appliances; car interior or exterior parts; articles for daily use; leisure goods; toys; stationery products; industrial goods; food manufacturing equipment; and medical devices.

[Medical Tube]

The medical tube of the present invention can be produced by molding the thermoplastic elastomer composition of the present invention according to a known molding method such as extrusion molding and injection molding. Alternatively, a blend obtained by dry-blending pellets of the component (A) and the component (B) directly in a single-screw extrusion molding machine, etc. may be extrusion-molded into a tube shape.

The processing conditions at the time of molding may be appropriately set but, usually, the melting temperature during molding is preferably from 150 to 250° C.; more preferably from 170 to 230° C.; and most preferably from 180 to 210° C. As other processing conditions, for example, the molding speed or the sizes of die and mandrel may be appropriately changed to preferable conditions.

The inner diameter, outer diameter, length, etc. of the medical tube are not limited and may be appropriately designed according to use. In addition, the tube is not limited to a single-layer tube and may be configured to have a multilayer structure with various resins. In the case of a multilayer tube, the thermoplastic elastomer composition of the present invention can be suitably used for all of an outer layer, an inner layer and an intermediate layer.

The medical tube of the present invention can be suitably used as a transfusion set tube, an extension tube, a medication tube, a blood circuit tube, a feeding tube, a connecting tube, a winged intravenous needle, an aspirating catheter, a drainage catheter, an enteral feeding catheter, a stomach tube catheter, a liquid medicine administering catheter, etc.

In this connection, with respect to the thermoplastic elastomer composition of the present invention constituting the medical tube of the present invention, the type, amount, configuration, etc. of each of the components (A) and (B) in the thermoplastic elastomer composition of the present invention can be identified by analyzing the medical tube by means of an analytical instrument such as gel permeation chromatography (GPC).

EXAMPLES

Specific embodiments of the present invention are described in greater detail below by referring to Examples. However, the present invention is not limited by the following Examples as long as the gist thereof is observed. In this connection, the values of various production conditions and evaluation results given in the following Examples mean preferable values of the upper limits or lower limits for embodiments of the present invention, and the preferable ranges may be a range specified by a combination between the upper-limit or lower-limit value described hereinabove and values in the following Examples or between values in the following Examples.

[Raw Material]

The materials used in Examples and Comparative Examples are shown below.

(Component (A))

<High-MFR Hydrogenated Block Copolymer>

A-1: "Kraton (registered trademark) MD 1648" produced by Kraton Polymer Corporation (hydrogenated product of styrene-butadiene-styrene block copolymer) [MFR (ISO 1133 (230° C., load: 2.16 kg)): 220 g/10 min, styrene unit content: 20% by mass, vinyl bond content in butadiene: 70% by mass]

<Low-MFR Hydrogenated Block Copolymer> a-1: "Hybrar (registered trademark) 7311F" produced by Kuraray Corporation (hydrogenated product of styrene-isoprene-styrene block copolymer) [MFR (ISO 1133 (230° C., load: 2.16 kg)): 2 g/10 min, styrene unit content: 12% by mass]

a-2: "Tuftec (registered trademark) H1221" by Asahi Kasei Corporation (hydrogenated product of styrene-butadiene-styrene block copolymer) [MFR (ISO 1133 (230° C., load: 2.16 kg)): 4.5 g/10 min, styrene unit content: 12% by mass, vinyl bond content in butadiene: 78% by mass]

a-3: "Hybrar (registered trademark) 7125F" produced by Kuraray Corporation (hydrogenated product of styrene-isoprene block copolymer) [MFR (ISO 1133 (230° C., load: 2.16 kg)): 4 g/10 min, styrene unit content: 12% by mass]

a-4: "Kraton (registered trademark) G1643MS" produced by Kraton Polymer Corporation (hydrogenated product of styrene-butadiene-styrene block copolymer) [MFR (ISO 1133 (230° C., load: 2.16 kg)): 18 g/10 min, styrene unit content: 18% by mass, vinyl bond content in butadiene: 70% by mass]

a-5: "Kraton (registered trademark) G1657MS" produced by Kraton Polymer Corporation (a mixture of 70% by mass of hydrogenated product of styrene-butadiene-styrene block copolymer and 30% by mass of hydrogenated product of styrene-butadiene block copolymer) [MFR (ISO 1133 (230° C., load: 5 kg)): 22 g/10 min, styrene unit content: 13% by mass, vinyl bond content in butadiene: 30% by mass]

(Component (B))

B-1: "RANPLEN SB-520Y" produced by Lotte Chemical Corporation (propylene-ethylene random copolymer) [MFR (JIS K7210:1999 (230° C., load: 2.16 kg)): 2.4 g/10 min, flexural modulus (JIS K7171:2008): 833 MPa)]

B-2: "WINTEC (registered trademark) WMG03" produced by Japan Polypropylene Corporation (propylene-ethylene random copolymer) [MFR (JIS K7210:1999 (230° C., load: 2.16 kg)): 30 g/10 min, flexural modulus (JIS K7171:2008): 1,250 MPa)]

B-3: "WINTEC (registered trademark) WFX6MC" produced by Japan Polypropylene Corporation (propylene-ethylene random copolymer) [MFR (JIS K7210:1999 (230° C., load: 2.16 kg)): 2 g/10 min, flexural modulus (JIS K7171:2008): 700 MPa)]

B-4: "WELNEX (registered trademark) RFG4MC" produced by Japan Polypropylene Corporation (propylene-ethylene random copolymer) [MFR (JIS K7210:1999 (230° C., load: 2.16 kg)): 6 g/10 min, flexural modulus (JIS K7171:2008): 280 MPa)]

B-5: "PWH00N" produced by SunAllomer Ltd. (propylene polymer) [MFR (JIS K7210:1999 (230° C., load: 2.16 kg)): 1,750 g/10 min, flexural modulus (JIS K7171:2008): 1,600 MPa)]

Examples 1 to 5 and Comparative Examples 1 to 7

Respective raw materials shown in Table-1 were charged into a same-direction twin-screw extruder ("PCM30-30-2V" manufactured by Ikegai Corp., cylinder bore diameter: 30 mm) at a rate of 10 kg/hour and melt-kneaded by raising the temperature in a range of 180 to 240° C. to produce pellets of thermoplastic elastomer composition.

The obtained pellets of thermoplastic elastomer composition were molded into a tube shape by using an extrusion molding machine ("PMS40-28" manufactured by IKG Corp.). The extrusion molding conditions were set to a die inner diameter: 3.85 mm, a mandrel outer diameter: 2.70 mm, a screw rotational speed: 10 rpm, a take-up speed: 3.5 m/min, and a resin temperature: from 180 to 210° C.

Using the obtained extruded tubes, evaluations of (1) and (2) below were performed. These evaluation results are shown in Table-1.

[Evaluation Method]

The evaluation methods for the extruded tube using the thermoplastic elastomer composition are as follows.

(1) Transparency (Surface Roughness)

The surface roughness (arithmetic average roughness Ra, ten-points average roughness Rz) of the extruded tube was measured using a surface roughness profilometer ("Surfcom 480A" manufactured by Tokyo Seimitsu Co., Ltd.). In the case where the value of surface roughness is large, light is likely to be diffusively reflected from the tube surface and therefore, the transparency of the tube is reduced. For use as a medical tube, in view of visibility of the contents, the transparency is preferably high, and it is preferred that Ra is 0.5 or less and Rz is 1 or less.

(2) Kink Resistance

The kink resistance (kink force, kink radius) of the extruded tube was measured using a tensile tester ("Autograph AG-2000A" manufactured by Shimadzu Corporation). Two plate-like jigs were provided in parallel on the tensile tester, and the extruded tube of 16 cm in length, which was curved into a U-shape, was fixed with a tape between jigs. The extruded tube was attached such that an about 5 cm portion on one end side runs along the plate surface of one jig; an about 5 cm portion on another end side runs along the plate surface of another jig, and the length of the tube in a semi-circular arc portion projecting from between jigs becomes 6 cm. The initial distance between two plate-like jigs was set to 60 mm. With bringing the jigs close to each other at a rate of 20 mm/min, the test force and the jig-to-jig distance were measured. Movement of the jigs was stopped when a kink in the tube was recognized. The maximum value of the test force was defined as the kink force, and the jig-to-jig distance when the test force took the maximum value was defined as the kink diameter.

For use as a medical tube, it is favorable that the force required to kinking is large and the kink diameter is small, and it is preferred that the test force at the time of kinking is 0.3 N or more and the kink diameter is 30 mm or less.

TABLE 1

|  |  |  | Example | | | | | Comparative Example | | | | | | |
| --- | --- | --- | --- | --- | --- | --- | --- | --- | --- | --- | --- | --- | --- | --- |
|  |  |  | 1 | 2 | 3 | 4 | 5 | 1 | 2 | 3 | 4 | 5 | 6 | 7 |
| Thermoplastic elastomer composition formulation (parts by mass)* | Component (A) hydrogenated block copolymer | A-1 | 38 | 38 | 33 | 16 | 33 | — | — | — | — | — | — | — |
|  |  | a-1 | 38 | 38 | 33 | 50 | 33 | 66 | — | — | — | — | 66 | 66 |
|  |  | a-2 | — | — | — | — | — | — | 66 | — | — | — | — | — |
|  |  | a-3 | — | — | — | — | — | — | — | 66 | — | — | — | — |
|  |  | a-4 | — | — | — | — | — | — | — | — | 66 | 76 | — | — |
|  |  | a-5 | — | — | 10 | 10 | — | 10 | 10 | 10 | 10 | — | 10 | 10 |

TABLE 1-continued

|  |  |  | Example | | | | | Comparative Example | | | | | | |
|---|---|---|---|---|---|---|---|---|---|---|---|---|---|---|
|  |  |  | 1 | 2 | 3 | 4 | 5 | 1 | 2 | 3 | 4 | 5 | 6 | 7 |
|  | Component (B) | B-1 | 9 | — | 9 | 9 | 12 | 9 | 9 | 9 | 9 | 9 | 9 | 9 |
|  | propylene polymer | B-2 | — | 9 | — | — | — | — | — | — | — | — | 11 | — |
|  |  | B-3 | 11 | 11 | 11 | 11 | 18 | 11 | 11 | 11 | 11 | 11 | — | — |
|  |  | B-4 | 4 | 4 | 4 | 4 | 4 | 4 | 4 | 4 | 4 | 4 | 4 | 4 |
|  |  | B-5 | — | — | — | — | — | — | — | — | — | — | — | 11 |
| Evaluation results | Transparency | Ra (μm) | 0.10 | 0.09 | 0.14 | 0.18 | 0.14 | 0.33 | 5.69 | 4.51 | 0.64 | 0.83 | 0.25 | 0.18 |
|  | (Surface roughness) | Rz (μm) | 0.45 | 0.41 | 0.72 | 0.74 | 0.98 | 1.40 | 20.90 | 16.17 | 2.56 | 3.07 | 1.60 | 1.14 |
|  | Kink resistance | Kink force (N) | 0.55 | 0.55 | 0.55 | 0.31 | 0.59 | 0.45 | 0.25 | 0.35 | 0.43 | 0.46 | 0.38 | 0.39 |
|  |  | Kink diameter (mm) | 25.67 | 22.92 | 27.17 | 18.81 | 27.29 | 26.48 | 25.18 | 25.51 | 38.85 | 33.28 | 22.44 | 22.23 |

*"—" in the column of thermoplastic elastomer composition formulation indicates that the component was not used.

As seen from Table-1, according to the thermoplastic elastomer composition of the present invention, a transparent medical tube having excellent kink resistance can be provided.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2016-242366) filed on Dec. 14, 2016, and the contents of which are incorporated herein by way of reference.

The invention claimed is:

1. A thermoplastic elastomer composition, comprising:
a hydrogenated block copolymer (A); and
a propylene polymer (B),
wherein the hydrogenated block copolymer (A) is a hydrogenated product of a block copolymer comprising first and second polymer blocks P comprising at least 50 mol % of an aromatic vinyl compound unit and a polymer block Q comprising at least 50 mol % of a conjugated diene,
wherein the hydrogenated block copolymer (A), before hydrogenation, has a formula (1):

P-Q-P     (1), wherein a total content of the aromatic vinyl compound unit in the hydrogenated block copolymer (A) is from 8 to less than 20 mass %, and
wherein the composition comprises, as the hydrogenated block copolymer (A), a high-MFR hydrogenated block copolymer having a melt flow rate (MFR) of 40 to 300 g/10 min as measured in accordance with ISO 1133 at 230° C. under a load of 2.16 kg.

2. The composition of claim 1, wherein the polymer block P comprises, in polymerized form, at least 50 mol % of styrene, and
wherein the polymer block Q comprises, in polymerized form, at least 50 mol % of butadiene, in the high-MFR hydrogenated block copolymer, and
wherein a proportion of 1,2-bond in the butadiene unit is 60% by weight or more.

3. The composition of claim 1, wherein the hydrogenated block copolymer (A) further comprises:
a low-MFR hydrogenated block copolymer having a melt flow rate (MFR) of 0.5 to 39 g/10 min as measured in accordance with ISO 1133 at 230° C. under a load of 2.16 kg.

4. The composition of claim 3, wherein a content of the low-MFR hydrogenated block copolymer per 100 parts by weight of the high-MFR hydrogenated block copolymer is from 10 to 500 parts by weight.

5. The composition of claim 1, wherein per 100 parts by weight of a total of the hydrogenated block copolymer (A) and the propylene polymer (B), a content of the hydrogenated block copolymer (A) is from 30 to 95 parts by weight and a content of the propylene polymer (B) is from 5 to 70 parts by weight.

6. The composition of claim 1, wherein 80 mol % or more of the conjugated diene compound units in the hydrogenated block copolymer (A) are hydrogenated.

7. The composition in claim 1, which is a molding material for a medical tube.

8. An extrusion molded body of the composition of claim 1.

9. The body of claim 8, which has a tube shape.

10. A medical tube, formed from the composition of claim 1.

11. The composition of claim 3, wherein the total content of the aromatic vinyl compound unit in the low-MFR hydrogenated block copolymer is less than 13 mass %.

12. The composition of claim 3, wherein the total content of the aromatic vinyl compound unit in the low-MFR hydrogenated block copolymer is no more than 12 mass %.

13. The composition of claim 1, wherein the aromatic vinyl compound comprises styrene.

14. The composition of claim 1, wherein the aromatic vinyl compound is styrene.

15. The composition of claim 1, wherein the aromatic vinyl compound comprises α-methylstyrene, p-methylstyrene, divinylbenzene, 1,1-diphenylethylene, N,N-dimethyl-p-aminoethyl styrene, and/or N,N-diethyl-p-aminoethylstyrene.

16. The composition of claim 1, wherein the polymer block (Q) in the hydrogenated block copolymer (A) is in a range of from 75 to 92 mass %.

17. The composition of claim 1, wherein the polymer block (Q) in the hydrogenated block copolymer (A) is in a range of from 80 to 91 mass %.

18. The composition of claim 1, wherein 85 mol % or more of the conjugated diene compound units in the hydrogenated block copolymer (A) are hydrogenated.

19. A thermoplastic elastomer composition, comprising:
a hydrogenated block copolymer component comprising (A) a high-MFR hydrogenated block copolymer of a structure P1-Q1-P1, (a1) a low-MFR hydrogenated block copolymer of a structure P2-Q2-P2, and optionally a second low-MFR hydrogenated block copolymer (a2) of a structure P3-Q3-P3; and
a propylene polymer (B),
wherein each hydrogenated block copolymer is a hydrogenated product of a block copolymer comprising respective first and second polymer blocks, P1, P2, and P3, comprising at least 50 mol % of an aromatic vinyl compound unit and a respective polymer block, Q1, Q2, and Q3, comprising at least 50 mol % of a conjugated diene,
wherein a total content of the aromatic vinyl compound unit in all of the hydrogenated block copolymers is from 8 to less than 20 mass %,
wherein the high-MFR hydrogenated block copolymer having a melt flow rate (MFR) of 40 to 300 g/10 min as measured in accordance with ISO 1133 at 230° C. under a load of 2.16 kg, and
wherein the first low-MFR hydrogenated block copolymer having a melt flow rate (MFR) of 0.5 to 39 g/10 min as measured in accordance with ISO 1133 at 230° C. under a load of 2.16 kg.

20. The composition of claim 19, wherein the hydrogenated block copolymer component comprise no further hydrogenated block copolymer beyond the high-MFR hydrogenated block copolymer (A), the low-MFR hydrogenated block copolymer (a1), and the second low-MFR hydrogenated block copolymer (a2).

* * * * *